(12) United States Patent
Horner et al.

(10) Patent No.: US 10,758,293 B2
(45) Date of Patent: Sep. 1, 2020

(54) SMOKE EVACUATION DEVICE INLET AND OUTLET MANIFOLDS

(71) Applicant: Megadyne Medical Products, Inc., Draper, UT (US)

(72) Inventors: Shawn K. Horner, Woods Cross, UT (US); Jason Harris, Lebanon, OH (US); Frederick Shelton, Hillsboro, OH (US); David Yates, West Chester, OH (US)

(73) Assignee: Megadyne Medical Products, Inc., Draper, UT (US)

(*) Notice: Subject to any disclaimer, the term of this patent is extended or adjusted under 35 U.S.C. 154(b) by 106 days.

(21) Appl. No.: 15/826,287

(22) Filed: Nov. 29, 2017

(65) Prior Publication Data

US 2019/0159826 A1    May 30, 2019

(51) Int. Cl.
*F04B 39/06* (2006.01)
*A61B 18/14* (2006.01)
(Continued)

(52) U.S. Cl.
CPC .......... *A61B 18/14* (2013.01); *B01D 46/0012* (2013.01); *B01D 46/0043* (2013.01); *B01D 46/4236* (2013.01); *B01D 46/4263* (2013.01); *F04B 39/0027* (2013.01); *F04B 39/06* (2013.01); *F04B 39/066* (2013.01); *F04B 49/22* (2013.01); *F04B 53/001* (2013.01);
(Continued)

(58) Field of Classification Search
CPC ............ B01D 46/4236; B01D 46/0012; B01D 46/4263; B01D 46/0043; B01D 2279/35; F04B 39/066; F04B 39/39; F04B 39/06; A61B 2218/008; A61B 2018/00601; A61B 2018/00595; A61B 18/1206
USPC ................. 55/385.1, 471; 96/380, 407, 418; 604/19–27, 35, 319
See application file for complete search history.

(56) References Cited

U.S. PATENT DOCUMENTS

| 1,165,288 A | 12/1915 | Rimmer |
| 1,789,194 A | 1/1931 | Rockwell |

(Continued)

FOREIGN PATENT DOCUMENTS

| GB | 2117982 | 10/1983 |
| PL | 220 478 | 10/2015 |

(Continued)

OTHER PUBLICATIONS

Bovie 35 hour filter found online [Sep. 11, 2018]—http://www.boviemedical.com/smoke-shark-ii/.

(Continued)

*Primary Examiner* — Minh Chau T Pham
(74) *Attorney, Agent, or Firm* — Workman Nydegger

(57) ABSTRACT

A smoke evacuation device includes one or more cooling mechanisms and an exhaust mechanism to reduce velocity and noise of filtered air exiting the smoke evacuation system. The cooling mechanism includes ventilation openings and/or a rotary mechanism disposed within the system to circulate air and cool by convective heat transfer. A pressure relief mechanism is also provided at the inlet or outlet of the system or the pump within the system. The pressure relief mechanism is configured to reduce pressures due to abnormal flows within the smoke evacuation system.

20 Claims, 7 Drawing Sheets

(51) Int. Cl.
  *B01D 46/00* (2006.01)
  *B01D 46/42* (2006.01)
  *F04B 53/00* (2006.01)
  *F04F 5/16* (2006.01)
  *F04B 49/22* (2006.01)
  *F04B 39/00* (2006.01)
  *A61B 18/12* (2006.01)
  *A61B 18/00* (2006.01)

(52) U.S. Cl.
  CPC ............ *F04F 5/16* (2013.01); *A61B 18/1206* (2013.01); *A61B 2018/00595* (2013.01); *A61B 2018/00601* (2013.01); *A61B 2218/008* (2013.01); *B01D 2279/35* (2013.01)

(56) References Cited

U.S. PATENT DOCUMENTS

| | | | |
|---|---|---|---|
| 2,577,606 A | 12/1951 | Conley | |
| 3,815,752 A | 6/1974 | Hoffman et al. | |
| 3,841,490 A | 10/1974 | Hoffman et al. | |
| 4,157,234 A | 6/1979 | Shaffer et al. | |
| 4,396,206 A | 8/1983 | Tsuge et al. | |
| 4,619,672 A | 10/1986 | Robertson | |
| 4,701,193 A * | 10/1987 | Robertson | A61M 1/0066 55/385.1 |
| 4,786,298 A | 11/1988 | Billet et al. | |
| 4,810,269 A | 3/1989 | Stackhouse et al. | |
| 4,826,513 A | 5/1989 | Stackhouse et al. | |
| 4,986,839 A | 1/1991 | Wertz et al. | |
| 5,108,389 A | 4/1992 | Comescu | |
| 5,144,176 A | 9/1992 | Popper | |
| 5,160,334 A | 11/1992 | Billings et al. | |
| 5,221,192 A | 6/1993 | Heflin et al. | |
| 5,226,939 A * | 7/1993 | Nicolas | A61B 18/00 55/309 |
| 5,242,474 A | 9/1993 | Herbst et al. | |
| 5,288,469 A | 2/1994 | Skalla et al. | |
| 5,318,516 A | 6/1994 | Comescu | |
| 5,336,218 A | 8/1994 | Linhares | |
| 5,342,349 A | 8/1994 | Kaufman | |
| 5,423,779 A | 6/1995 | Yeh | |
| 5,431,650 A | 7/1995 | Comescu | |
| 5,522,808 A | 6/1996 | Skalla | |
| 5,597,385 A | 1/1997 | Moerke | |
| 5,620,441 A | 4/1997 | Greff et al. | |
| 5,674,219 A | 10/1997 | Monson et al. | |
| 5,690,480 A | 11/1997 | Suzuki et al. | |
| 5,853,410 A | 12/1998 | Greff et al. | |
| 5,874,052 A | 2/1999 | Holland | |
| 5,910,291 A | 6/1999 | Skalla et al. | |
| 5,992,413 A | 11/1999 | Martin et al. | |
| 6,050,792 A | 4/2000 | Shaffer | |
| 6,110,259 A | 8/2000 | Schultz et al. | |
| 6,129,530 A | 10/2000 | Shaffer | |
| 6,203,590 B1 | 3/2001 | Byrd | |
| 6,203,762 B1 | 3/2001 | Skalla et al. | |
| 6,439,864 B1 | 8/2002 | Shaffer | |
| 6,511,308 B2 | 1/2003 | Shaffer | |
| 6,524,307 B1 | 2/2003 | Palmerton et al. | |
| 6,544,210 B1 | 4/2003 | Trudel et al. | |
| 6,585,791 B1 | 7/2003 | Garito et al. | |
| 6,589,316 B1 | 7/2003 | Schultz et al. | |
| 6,592,543 B1 | 7/2003 | Wortrich et al. | |
| 6,616,722 B1 | 9/2003 | Cartellone | |
| 6,663,698 B2 | 12/2003 | Mishin et al. | |
| D485,339 S | 1/2004 | Klug | |
| 6,709,248 B2 | 3/2004 | Fujioka et al. | |
| 6,736,620 B2 | 5/2004 | Satoh | |
| 6,758,885 B2 | 7/2004 | Leffel et al. | |
| 6,786,707 B2 | 9/2004 | Kim | |
| D513,314 S | 12/2005 | Iddings | |
| 7,014,434 B2 | 3/2006 | Fujioka et al. | |
| D521,137 S | 5/2006 | Khalil | |
| D545,955 S | 7/2007 | Arlas | |
| 7,258,712 B2 | 8/2007 | Schultz et al. | |
| 7,276,052 B2 | 10/2007 | Kobayashi et al. | |
| D555,803 S | 11/2007 | Galrto | |
| 7,294,116 B1 * | 11/2007 | Ellman | A61B 18/00 24/170 |
| 7,465,156 B2 | 12/2008 | Lee | |
| 7,497,340 B2 | 3/2009 | Hershberger et al. | |
| 7,597,731 B2 | 10/2009 | Palmerton | |
| D625,399 S | 10/2010 | Horiguchi | |
| D626,204 S | 10/2010 | Morgan | |
| 7,819,957 B2 | 10/2010 | Roberts et al. | |
| 7,942,655 B2 | 5/2011 | Shaffer | |
| 8,033,798 B2 | 10/2011 | Suh et al. | |
| 8,142,175 B2 | 3/2012 | Duppert et al. | |
| 8,190,398 B2 | 5/2012 | Kitaguchi et al. | |
| D666,704 S | 9/2012 | Osendorf | |
| 8,298,420 B2 | 10/2012 | Burrows | |
| 8,608,816 B2 | 12/2013 | Palmerton et al. | |
| 8,684,705 B2 | 4/2014 | Magoon et al. | |
| 8,727,744 B2 | 5/2014 | Magoon et al. | |
| 8,974,569 B2 * | 3/2015 | Matula | A61M 13/003 210/295 |
| 9,011,366 B2 | 4/2015 | Dean et al. | |
| 9,028,230 B2 | 5/2015 | Shaffer | |
| 9,067,030 B2 | 6/2015 | Stearns et al. | |
| 9,074,598 B2 | 7/2015 | Shaffer et al. | |
| 9,199,047 B2 | 12/2015 | Stearns et al. | |
| 9,215,964 B2 | 12/2015 | Loske | |
| 9,366,254 B2 | 6/2016 | Murakami | |
| 9,387,295 B1 | 7/2016 | Mastri et al. | |
| 9,387,296 B1 | 7/2016 | Mastri et al. | |
| D764,649 S | 8/2016 | Ko | |
| 9,415,160 B2 | 8/2016 | Bonano et al. | |
| 9,435,339 B2 | 9/2016 | Calhoun et al. | |
| 9,474,512 B2 | 10/2016 | Blackhurst et al. | |
| 9,532,843 B2 | 1/2017 | Palmerton | |
| 9,549,849 B2 | 1/2017 | Charles | |
| 9,579,428 B1 | 2/2017 | Reasoner et al. | |
| D802,024 S | 11/2017 | Aoki | |
| 9,867,914 B2 * | 1/2018 | Bonano | A61M 1/0001 |
| 2004/0223859 A1 | 11/2004 | Sharp | |
| 2005/0000196 A1 | 1/2005 | Schultz | |
| 2005/0189283 A1 | 9/2005 | Smit et al. | |
| 2006/0099096 A1 | 5/2006 | Shaffer et al. | |
| 2007/0066970 A1 | 3/2007 | Ineson | |
| 2009/0022613 A1 | 1/2009 | Dai et al. | |
| 2010/0185139 A1 * | 7/2010 | Stearns | A61M 13/003 604/26 |
| 2013/0231606 A1 * | 9/2013 | Stearns | A61B 17/3421 604/26 |
| 2014/0356207 A1 | 12/2014 | Yang | |
| 2015/0224237 A1 | 8/2015 | Reasoner et al. | |
| 2015/0273381 A1 | 10/2015 | Stoner et al. | |
| 2016/0000494 A1 | 1/2016 | Comescu | |
| 2016/0001102 A1 | 1/2016 | Huh | |
| 2016/0287817 A1 | 10/2016 | Mastri et al. | |
| 2016/0367266 A1 | 12/2016 | Palmerton et al. | |
| 2017/0014557 A1 | 1/2017 | Minskoff et al. | |
| 2017/0014560 A1 * | 1/2017 | Minskoff | A61M 1/0027 |
| 2017/0165725 A1 | 6/2017 | Hersey et al. | |
| 2017/0181768 A1 | 6/2017 | Galley | |
| 2019/0159830 A1 | 5/2019 | Horner et al. | |

FOREIGN PATENT DOCUMENTS

| | | |
|---|---|---|
| WO | 9408698 | 4/1994 |
| WO | 2016142690 | 9/2016 |
| WO | 201703712 | 1/2017 |
| WO | 2017112684 | 6/2017 |

OTHER PUBLICATIONS

"Megadyne Surgical Smoke Evacuation System found online [Sep. 11, 2018]—http://www.hcp-austria.com/Minivac%20Smoke%20Evacuators.html".

Non-Final Office Action for U.S. Appl. No. 29/627,793 dated Oct. 29, 2018.

(56) References Cited

OTHER PUBLICATIONS

International Search and Written Opinion for PCT/IB2018/059376 dated May 7, 2019.

* cited by examiner

SMOKE EVACUATION DEVICE INLET AND OUTLET MANIFOLDS

BACKGROUND

1. Technical Field

The present disclosure relates to smoke evacuation systems used in electrosurgical systems. More specifically, the present disclosure relates to smoke evacuation system inlet and outlet manifolds.

2. The Relevant Technology

As is known to those skilled in the art, modern surgical techniques typically employ radio frequency (RF) power to cut tissue and coagulate bleeding encountered in performing surgical procedures. Such electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cauterization results in smoke released into the air that can be distracting or otherwise unpleasant. Many electrosurgical systems may therefore employ an evacuation system that captures the resulting smoke and directs it through a filter and exhaust port, away from practitioners and/or patients. A smoke evacuation system typically creates suction directed at the smoke using fans to draw the smoke through a tube connecting the surgical instrument to an exhaust port.

Smoke evacuation systems typically comprise a pump and a filter. The pump creates suction that draws smoke through a vacuum tube into the filter. A vacuum tube may terminate at the hand piece that includes the electrode tip so that the smoke is sucked in at the hand piece. Other electrosurgical systems may include separate hand pieces that are used to suck the smoke into the system. The smoke travels to the filter via a vacuum tube and offensive smells are filtered out as the smoke moves through the filter. Filtered air may then exit the smoke evacuation system as exhaust.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to smoke evacuation systems used in electrosurgical systems. Specifically, the present disclosure relates to apparatuses and methods for reducing noise associated with typical smoke evacuation systems. The present disclosure also relates to apparatuses and methods for controlling air flow parameters to cool the smoke evacuation system in order to avoid overheating.

In one embodiment, a smoke evacuation system includes a housing surrounding an enclosure and an airflow path extending inside the enclosure from an inlet port to an outlet port of the smoke evacuation system. The system also includes a motor and pump disposed within the enclosure. A cooling mechanism is configured to induce airflow through the enclosure to cool the enclosure. The induce airflow is proportionate to the work output of the motor.

In one embodiment, a smoke evacuation system includes an inlet port, outlet port, an airflow path extending between the inlet port and the outlet port, and one or more cooling vents. The smoke evacuation system also includes an exhaust mechanism near the outlet port. The exhaust mechanism is configured to diffuse air exiting at the outlet port.

In one embodiment, a smoke evacuation system includes an airflow control mechanism, an exhaust diffuser, and a rotary mechanism. The airflow control mechanism reduces a pressure within the smoke evacuation system when abnormal flow or high pressures are detected. The exhaust diffuser reduces the exit noise of the filtered air without baffling or redirecting flow causing an exit head pressure. The rotary mechanism induces an airflow through the smoke evacuation system at a flow rate that is proportional to the rate at which a pump is pumping filtered air through the smoke evacuation system.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present disclosure relates to smoke evacuation systems used in electrosurgical systems. Specifically, the present disclosure relates to apparatuses and methods for reducing noise associated with typical smoke evacuation systems. The present disclosure also relates to apparatuses and methods for controlling air flow parameters to cool the smoke evacuation system in order to avoid overheating.

Figure 1:
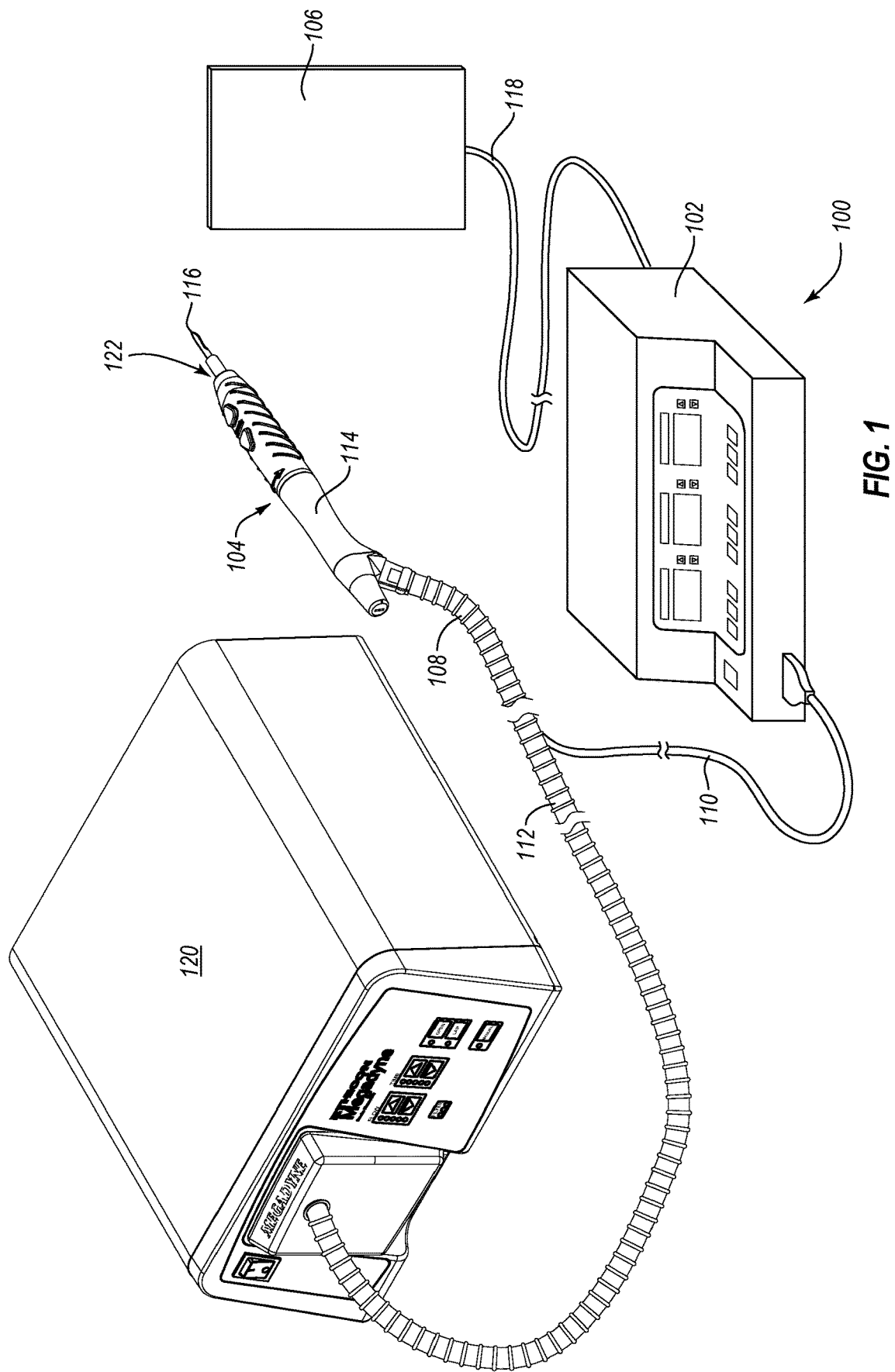
FIG. 1 illustrates an embodiment of an electrosurgical system.

FIG. 1 illustrates an exemplary electrosurgical system 100. The illustrated embodiment includes a signal generator 102, an electrosurgical instrument 104, a return electrode 106, and a smoke evacuation system 120. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site.

Generally, electrosurgical instrument 104 includes a handpiece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with or adjacent to electrode tip 116. The tissue heating takes place at an appropriately high temperature to allow electrosurgical instrument 104 to be used to perform electrosurgery. Return electrode 106 is connected to generator 102 by a cable 118, and is either applied to or placed in close proximity to the patient (depending on the type of return electrode), in order to complete the circuit and provide a return electrical path to wave generator 102 for energy that passes into the patient's body.

The heating of cellular matter of the patient by the electrode tip 116, or cauterization of blood vessels to prevent bleeding, results in smoke being released where the cauterization takes place. The electrosurgical instrument 104 may comprise a smoke evacuation conduit opening 122 near the electrode tip 116 so as to be able to capture the smoke that is released during a procedure. Vacuum suction may draw the smoke into the conduit opening 122, through the electrosurgical instrument 104, and into the vacuum hose 112 toward the smoke evacuation system 120.

Figure 2:
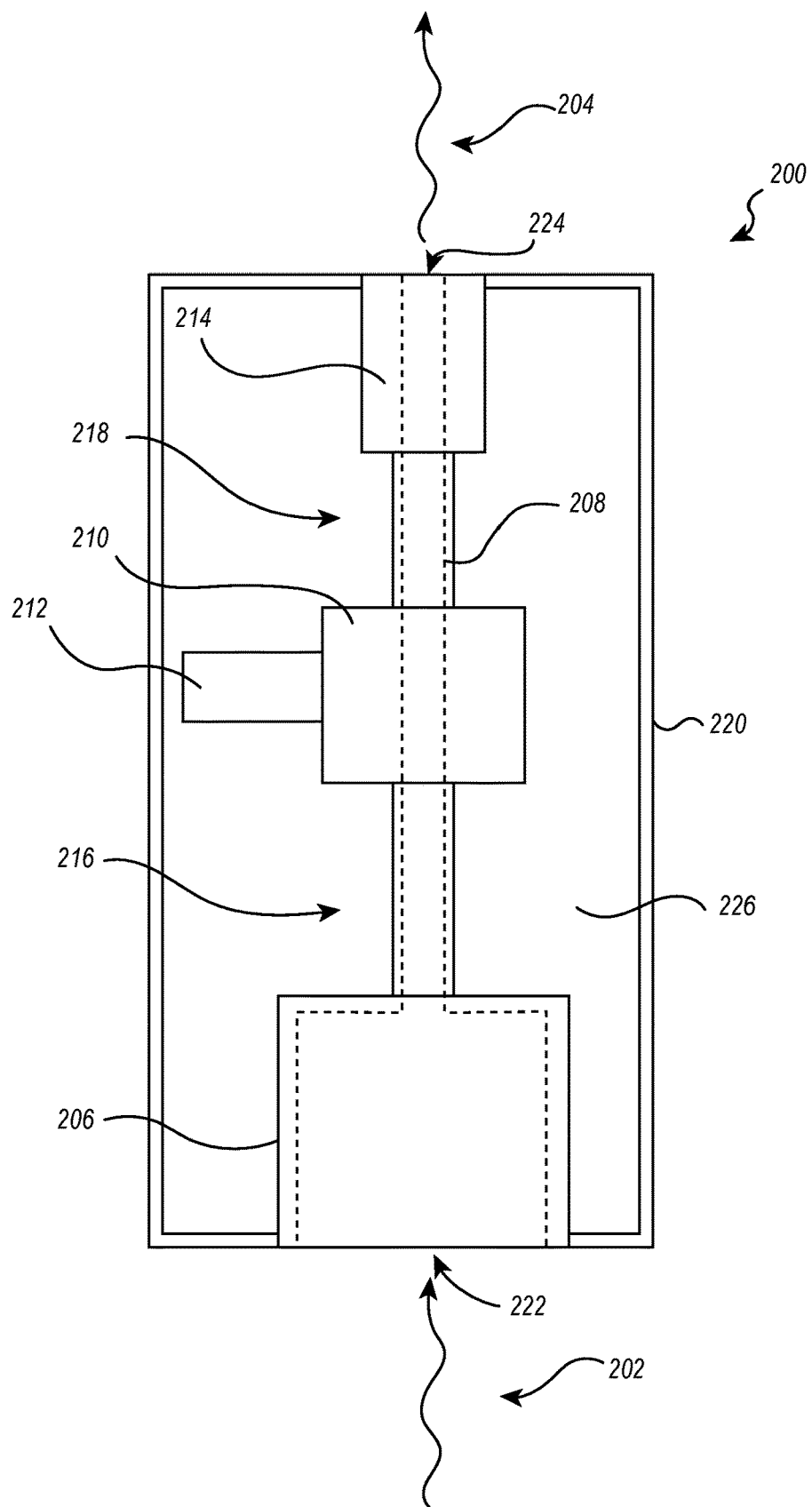
FIG. 2 illustrates a schematic of a smoke evacuation system.

FIG. 2 illustrates an embodiment of a smoke evacuation system 200. The smoke evacuation system 200 may include a filter 206 and an airflow path 208. The airflow path 208 may comprise a pump 210 disposed in-line with the airflow path 208 producing a pressure difference within the airflow path 208 by mechanical action. The term "pump" as used herein refers to blowers, compressors, and other mechanical means of moving a fluid/gas while increasing the pressure of the fluid/gas. This pressure difference may cause movement of a gas through the airflow path 208. The gas drawn through the airflow path 208 may be smoke 202, or the filtered air remaining after the smoke 202 has passed through the filter 206. A motor 212 drives the pump 210. The smoke evacuation system 200 may also include an exhaust mechanism 214 that may also be disposed in-line with the airflow path 208.

The airflow path 208 may be disposed between an inlet port 222 and an outlet port 224. The smoke 202 may flow into the filter 206 at the inlet port 222, be pumped through the airflow path 208 by the pump 210 so that the smoke 202 is drawn through the filter 206, through the exhaust mechanism 214, and out the outlet port 224 of the smoke evacuation system 200. The air exiting the smoke evacuation system 200 at the outlet port 224 may be the exhaust 204. The exhaust 204 may consist of filtered air/gas that has passed through the smoke evacuation system 200 and exits through the outlet port 224.

The airflow path 208 may comprise a first zone 216 and a second zone 218. The first zone 216 may be upstream from the pump 205 and the second zone 218 may be downstream from the pump 205. The pump 205 may pressurize the air in the airflow path 208 so that the air in the second zone 218 has a higher pressure than the air in the first zone 216. This pressure difference causes air to flow through the airflow path 208 from the inlet port 222 to the outlet port 224.

The smoke evacuation system 200 may also include a housing 220. FIG. 2 illustrates a schematic view of a smoke evacuation system 200 to show the various components within the housing 220. An enclosure 226 may be defined by the space inside the housing 220 but outside the airflow path 208. The housing 220 may completely or partially encompass or enclose the smoke evacuation system 200. The airflow path 208 may be at least partially comprised of a tube or other conduit that substantially contains and/or isolates the air moving through the airflow path 208 air outside the airflow path 208.

For example, the first zone 216 of the airflow path 208 may comprise a tube through which the airflow path 208 extends between the filter 206 and the pump 210. The second zone 218 of the airflow path 208 may also comprise a tube through which the airflow path 208 extends between the pump 210 and the exhaust mechanism 214. The airflow path 208 also extends through the filter 206, pump 210, and exhaust mechanism 214 so that a continuous airflow path 208 extends from the inlet port 222 to the outlet port 224.

Figure 3A:
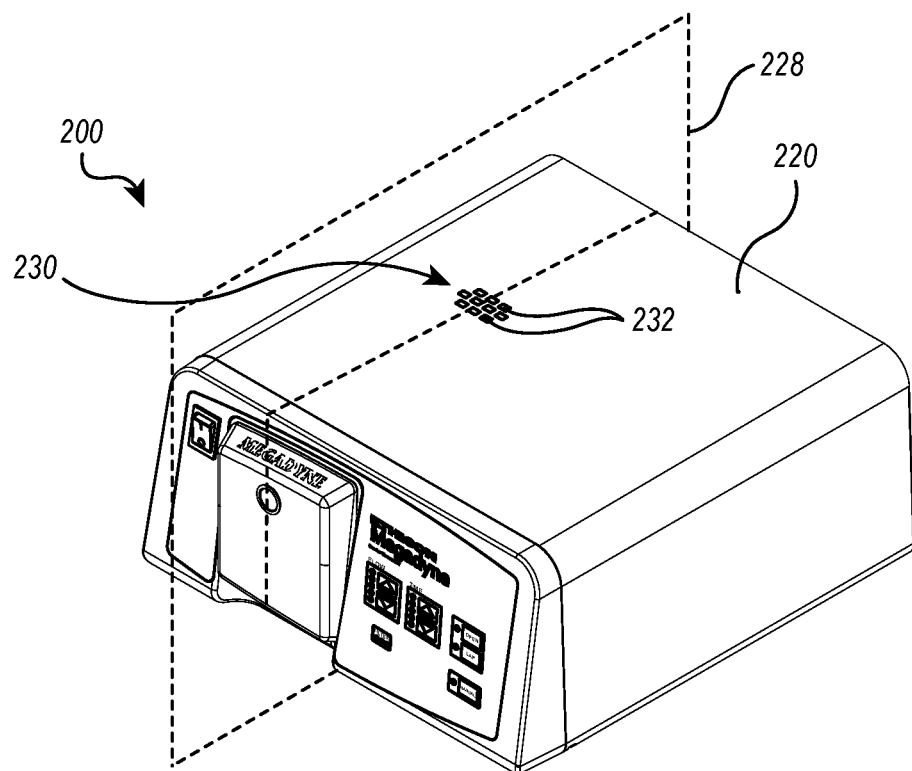
FIG. 3A illustrates a perspective view of an embodiment of a smoke evacuation system.

FIG. 3A illustrates a smoke evacuation system 200 that includes a cooling mechanism 230. The cooling mechanism 230 may include a plurality of openings 232 in the outer housing 220 of the smoke evacuation system 200. The embodiment illustrated in FIG. 3A includes ten square-shaped openings 232 disposed together in a group. Air may flow into the smoke evacuation system 200 through the openings 232 in the outer housing 220. Air that enters through the openings 232 may cool internal components of the smoke evacuation system 200, such as the motor and/or pump, by convective heat transfer.

Other embodiments of a smoke evacuation system 200 may include cooling mechanisms 230 that have more or less than ten openings 232. For example, one embodiment may include only one opening 232. Other embodiments may include more than ten openings 232. It will be appreciated that a large number of variations in the openings 232 in the outer housing 220, including the size, shape, and number of openings 232, may be employed in other embodiments to achieve the same or similar cooling effects of the openings 232.

The openings 232 may be positioned in the outer housing 220 to facilitate cooling of certain components within the outer housing 220. For example, in the embodiment illustrated in FIG. 3A, the openings 232 are positioned such that they may be directly over a motor (e.g., motor 212 in FIG. 2) inside the outer housing 220. In other embodiments, the openings 232 may be positioned elsewhere to correspond with a motor that may be at a different location inside the outer housing 220. The openings may be place on the top, bottom and/or side surfaces of the outer housing 220. One will appreciate that the openings 232 may be strategically place anywhere in the outer housing 220 to facilitate convective cooling of the various components inside the outer housing 220.

Figure 3B:
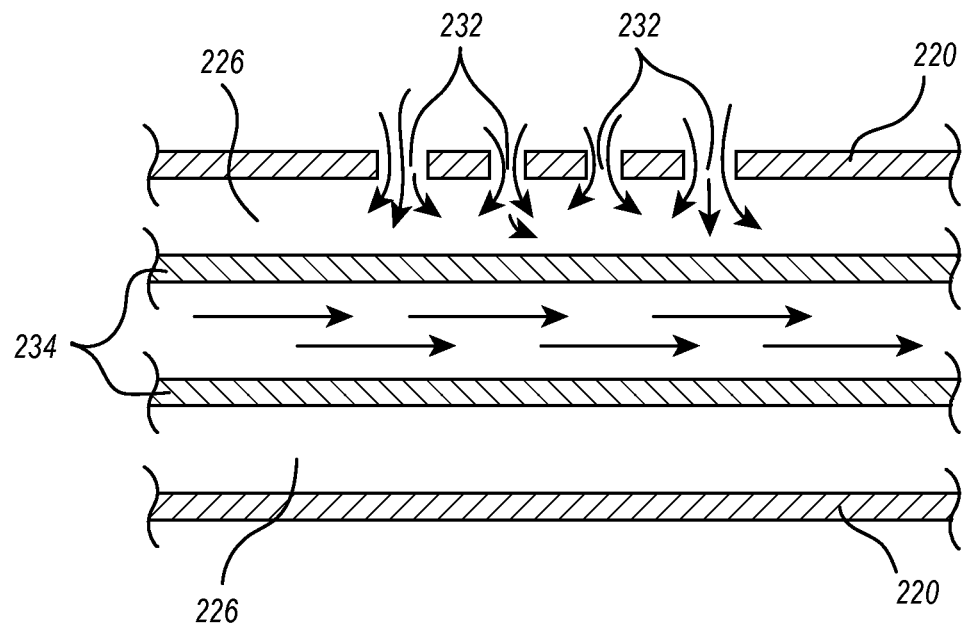
FIG. 3B illustrates a partial cross-sectional view of the smoke evacuation system illustrated in FIG. 3A.

FIG. 3B illustrates a partial cross-sectional view of the smoke evacuation system 200 of FIG. 3A on plane 228. The arrows in FIG. 3B indicate airflow. Air may flow inside the airflow path 208 of the smoke evacuation system 200 through a tube 234 and the various components that form or define the airflow path 208, such as the filter 206, pump 210, and exhaust mechanism 214. Air from outside the outer housing 220 may flow into the enclosure 226 of the smoke evacuation system 200 through the openings 232, as indicated by the arrows through the openings 232. In the illustrated embodiment, the air flowing through airflow path 208 may be sealed off from the air entering through the openings 232 so that no mixing occurs. The air entering through the openings 232 may cool the motor 215, pump 210, exhaust mechanism 214, tube 234 or other components the air comes into contact with by convective heat transfer. These components may also be cooled when hot air within the enclosure escapes out of the openings 232.

Figure 4:
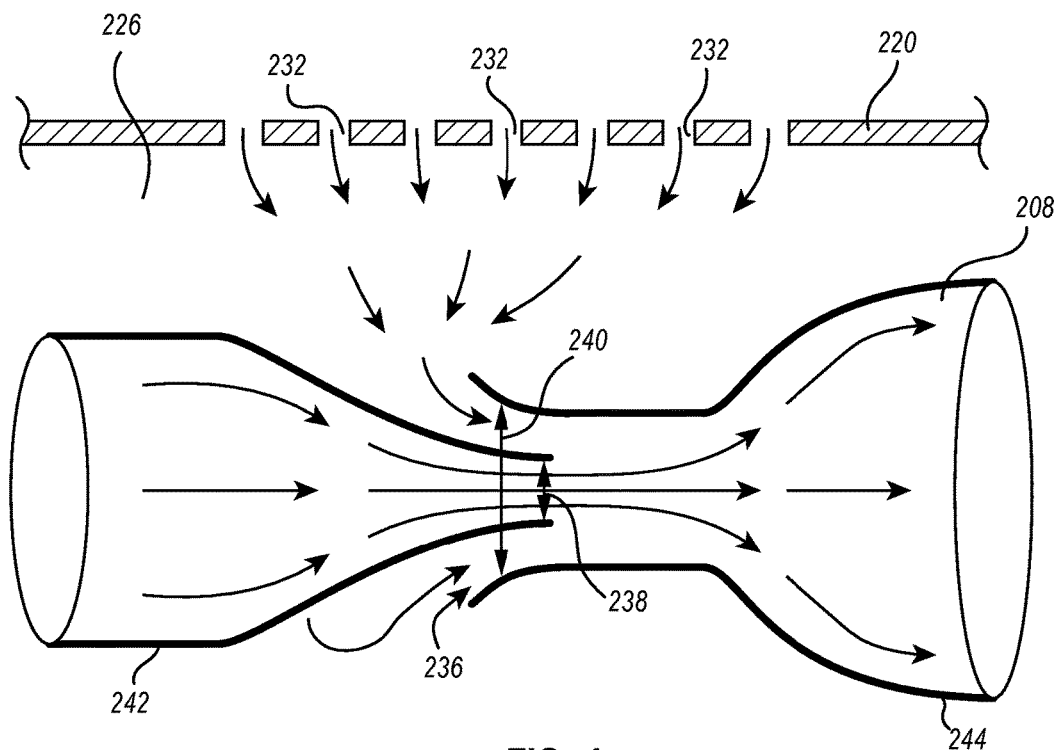
FIG. 4 illustrates a partial cross-sectional view of an embodiment of a cooling mechanism.

Alternatively, in another embodiment illustrated in FIG. 4, the air flowing through the airflow path 208 may not be sealed off from air entering the smoke evacuation system 200 through the openings 232 in the outer housing 220. In this embodiment, the air entering through the openings 232 may enter into the airflow path 208 to mix with the air flowing through the airflow path 208. This mixing may cause the air flowing inside the airflow path 208 to be cooled by the air flowing into the airflow path 208 through the openings 232 in the outer housing 220.

One or more airflow path openings 236 may be provided in the airflow path 208 so that air from outside the airflow path 208 may enter into the airflow path 208. In one embodiment, the opening may be an open juncture 236 between a first portion of the airflow path 242 and a second portion of the airflow path 430. The first portion 242 may extend into a second portion 244. The first portion 242 may have a first diameter 238 and the second portion 244 may have a second diameter 240. The first diameter 236 may be smaller than the second diameter 240. The first portion 242 may extend at least partially into the second portion 244 so that the second portion 244 at least partially receives the first portion 242. In this configuration, substantially all of the air flowing through the airflow path 208 may remain inside the airflow path 208 as it flows from the first portion 242 to the second portion 244.

As the air within the airflow path 208 flows from the first portion 242 to the second portion 244, a suction may be created that draws air from outside the airflow path 208 into the airflow path 208. In this way, air from outside the outer housing 220 may enter into the outer housing 220 through the openings 232 in the outer housing 220 and enter the airflow path 208 through the one or more open junctures 236 to mix with air flowing inside the airflow path 208. This mixing may cause the airflow path 208 or other components, such as the pump 210 and/or motor 212, to be cooled.

For example, after the air is mixed and cooled within the airflow path 208 according to the embodiment illustrated in FIG. 4, the cooled air may then pass through the pump 210. Also for example, air that enters the smoke evacuation system 200, but does not mix with the air inside the airflow path 208, may freely flow within the outer housing 220 so that it flows over/around the motor 212, causing the motor 212 to be cooled.

The embodiment illustrated in FIG. 4 illustrates an airflow path 208 that includes one open juncture 236 in the airflow path 208 through which air may enter. Other embodiments may include more than one airflow path openings 210. For example, one embodiment may include two or more open junctures 236 disposed in series along the airflow path 208. Increasing the number of open junctures 236 may increase the mixing of air from outside the airflow path 208 with air inside the airflow path 208 to increase cooling capacity.

Figure 5A:
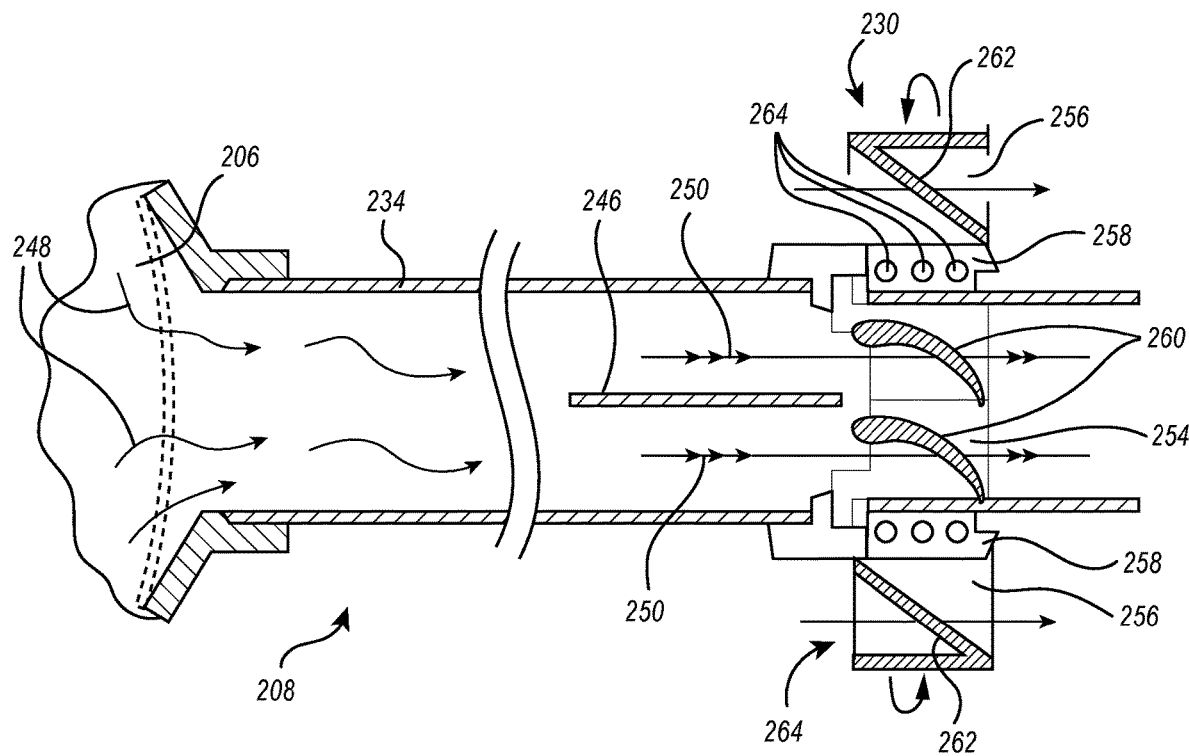
FIG. 5A illustrates a cross-sectional view of an embodiment of a cooling mechanism.

FIG. 5A illustrates an embodiment of an airflow path 208 that has a cooling mechanism 230. The airflow path 208 may be comprised of a tube 234 or other conduit through which air may flow. The air is indicated by the arrows in the airflow path 208. The airflow path may also include one or more interior walls 246 configured to straighten or direct the airflow. Air exiting the filter 206, indicated by arrows 248, may be flowing turbulently. The one or more walls 246 may create channels that direct air 250 in the downstream direction, as indicated by arrows 250, resulting in more laminar flow.

Figure 5B:
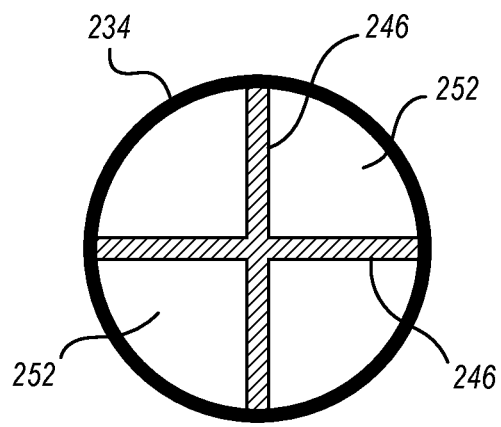
FIG. 5B illustrates a front view of an embodiment of an airflow path.

FIG. 5B illustrates a cross sectional view of the airflow path 208 where the one or more walls 246 are located in FIG. 5A. The one or more walls 246 may create one or more channels 252 through which the air 250 may flow. The channels may be bounded by the one or more walls 252 and the tube 234 or other conduit of the airflow path 208. Other embodiments may include one or more walls 246 that create more or less than the four channels 252 illustrated in FIG. 5B. Other embodiments may also include one or more walls 246 that create channels 252 having various shaped cross-sections, such as circular, square, or other shaped cross-sections.

Referring back to FIG. 5A, the cooling mechanism 230 may include a first rotary element 254 coupled to a second rotary element 256 via a rotary element coupler 258. The first rotary element 254 may comprise a plurality of first rotary element blades 260 and the second rotary element 256 may comprise a plurality of second rotary element blades 262. The second rotary element 256 may be disposed outside and surrounding the tube 234 of the airflow path 208 and inside the enclosure 226 of the smoke evacuation system 200. The first rotary element 254 may be disposed within the tube 234 of the airflow path 208.

As noted, the first and second rotary elements 254, 256 may be coupled by a rotary element coupler 258 so that rotation of the first rotary element 254 causes the rotation of the second rotary element 256. For example, air 250 flowing through the airflow path 208 may push against the first rotary element blades 260 causing the first rotary element 254 to rotate. The rotation of the first rotary element 254, which is coupled to the second rotary element 256, may cause the second rotary element 256 to rotate as well.

Figure 5C:
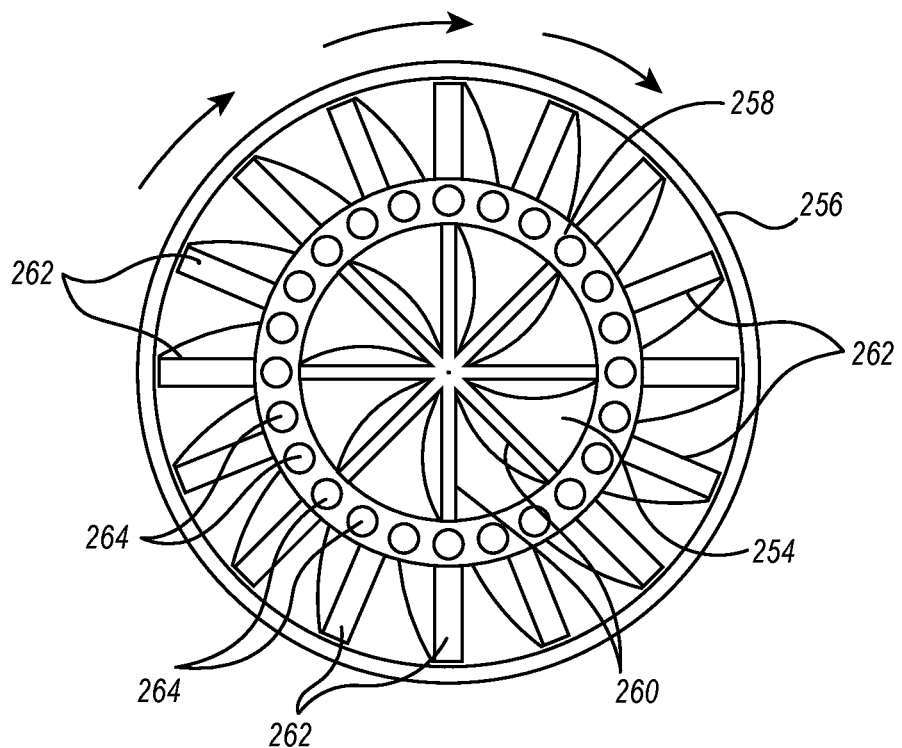
FIG. 5C illustrates a front view of the cooling mechanism illustrated in FIG. 5A.

The rotary element coupler 258 may be disposed in-line with the airflow path 208 so that air does not escape the airflow path 208 at the rotary element coupler 258. The rotary element coupler 258 may rotate with the first rotary element 254 and therefore may comprise a plurality of ball bearings 264 to reduce frictional resistance to rotation while maintaining a tight fit within the airflow path 208 to avoid leaking. In this way, the rotary element coupler 258 may also be integrated into the tube 234 of the airflow path 208 to maintain a sealed path for air to flow within the airflow path 208. FIG. 5C illustrates a front cross-sectional view of the first rotary element 254, second rotary element 256, and rotary element coupler 258 with ball bearings 264 for further reference.

The second rotary element blades 262 may move air in the enclosure 226 to flow to and/or around other components inside the enclosure 226. For example, a motor 212 may be disposed within the enclosure 226. The motor may drive the pump 210 to create a flow of air 248, 250 through the airflow path 208. The air 248 may flow through the first rotary element 254, causing the first and second rotary elements 254, 256 to rotate as discussed above. The second rotary element 256 may move air that has been drawn into the enclosure 226 from outside the enclosure 226, as described above, and circulate the air throughout the enclosure 226. The circulating air may cool the motor 212 by convective heat transfer.

Therefore, the cooling capacity of the circulated air pushed by the second rotary element 256 may be proportional to the work of the motor 212. For example, the more work output by the motor 212, the greater the rate of the airflow through the airflow path 208 may be. A greater rate of airflow may result in a greater velocity of circulated air pushed throughout the enclosure 226 by the second rotary element 256. Therefore, the more work produced by the motor 212, the greater the cooling capacity of the cooling mechanism 230 may be. The cooling mechanism 230 may also be configured to cool other components within the enclosure 226, such as the pump 210.

Figure 6:
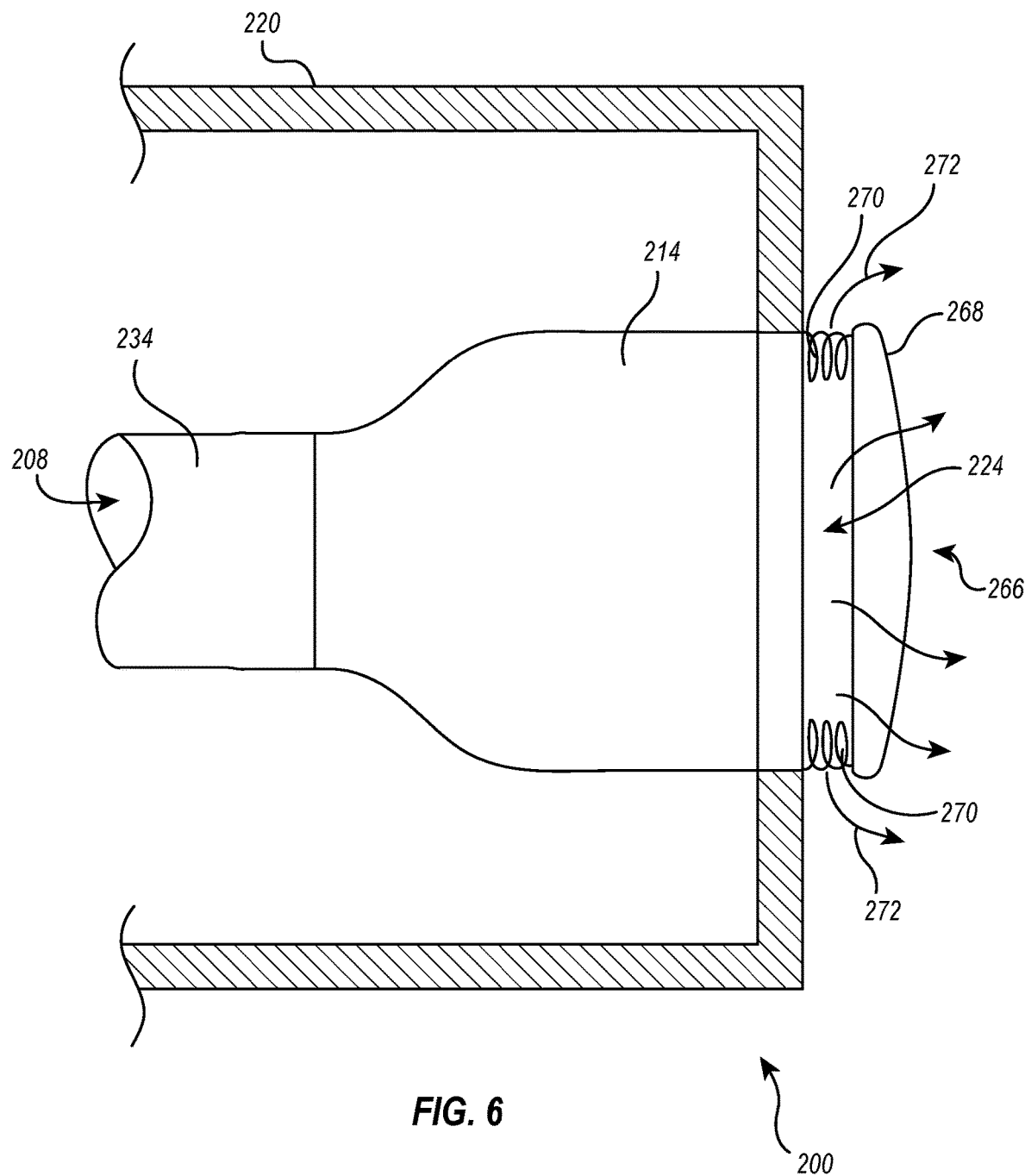
FIG. 6 illustrates an embodiment of an exhaust mechanism and a pressure relief mechanism disposed at an outlet port of a smoke evacuation system.

FIG. 6 illustrates an embodiment of an exhaust mechanism 214 disposed within the outer housing 220 near or at the outlet port 224. The exhaust mechanism 214 may include a pressure relief mechanism 266 disposed at the outlet port 224 of the smoke evacuation system 200. The exhaust port 266 may be connected with the tube 230 or other conduit through which air flows in the airflow path 208. The air flowing through the airflow path 208 may be pressurized by the pump 210 illustrated in FIG. 2. The pressure relief mechanism 266 may limit the suction of the smoke evacuation system 200 when abnormal flow or high pressure is detected within the airflow path 208.

The pressure release mechanism 266 may comprise an outlet port cover 268 disposed over the outlet port 224. The cover 268 may be secured over the outlet port 224 via one or more biasing members 270. In the illustrated embodiment, the one or more biasing members 272 are coil springs. Other types of biasing members 270 may be used in other embodiments or in combination with the springs illustrated in FIG. 6. The biasing springs 268 may hold the cover 268 away from the outlet port 224 so that filtered air 272 may exit out of the outlet port 224. As pressure within the airflow path 208 increases, the one or more biasing members 270 may extend so that the cover is further away from the outlet port 224 to increase airflow out of the outlet port 224. Increasing airflow out of the outlet port may decrease a pressure within the airflow path 208.

In this way, the pressure release mechanism 266 may limit the pressure within the airflow path 208 by increasing airflow out of the outlet port 224. A pressure limit, which depends on the biasing force of the biasing members 270, may therefore not be exceeded within the airflow path 208. A similar pressure release mechanism may also be disposed at the inlet port 222 of the smoke evacuation system 200 to regulate a pressure within the airflow path 208. It will also be appreciated that a similar pressure release mechanism may be disposed anywhere along the airflow path 208 to accomplish the same objective of relieving pressure in the system. For example, a pressure release mechanism may be disposed at an inlet or outlet of the pump 210.

It will be appreciated that other embodiments of a pressure relief mechanism may be employed to ensure that a pressure limit is not exceeded within the smoke evacuation system 200. For example, any mechanism that increases airflow out of the outlet port 224 or pump outlet, proportional to an increased pressure in the airflow path 208, may be suitable. Likewise, any mechanism that decreases airflow into the system at the inlet port 222 or pump inlet, proportional to an increase in pressure detected within the airflow path 208, may also be suitable.

For example, one embodiment of a pressure relief mechanism may include a controller and a pressure sensor. The pressure sensor may signal the controller to activate a mechanism that increases or decreases flow in or out of the smoke evacuation system similar to the pressure relief mechanisms described above. A pressure limit may be pre-determined and set so that when the sensor senses a pressure within the smoke evacuation system that is equal to or greater than the pressure limit, the pressure relief mechanism is activated by the controller.

Figure 7A:
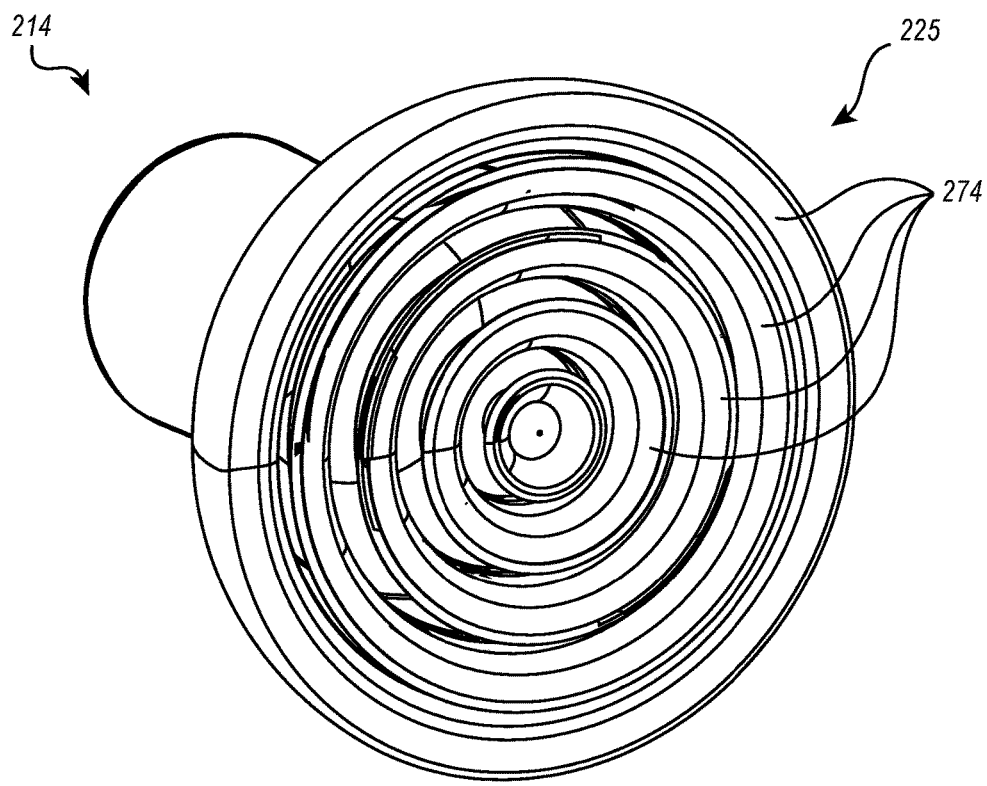
FIG. 7A illustrates a perspective view of a diffuser.
Figure 7B:
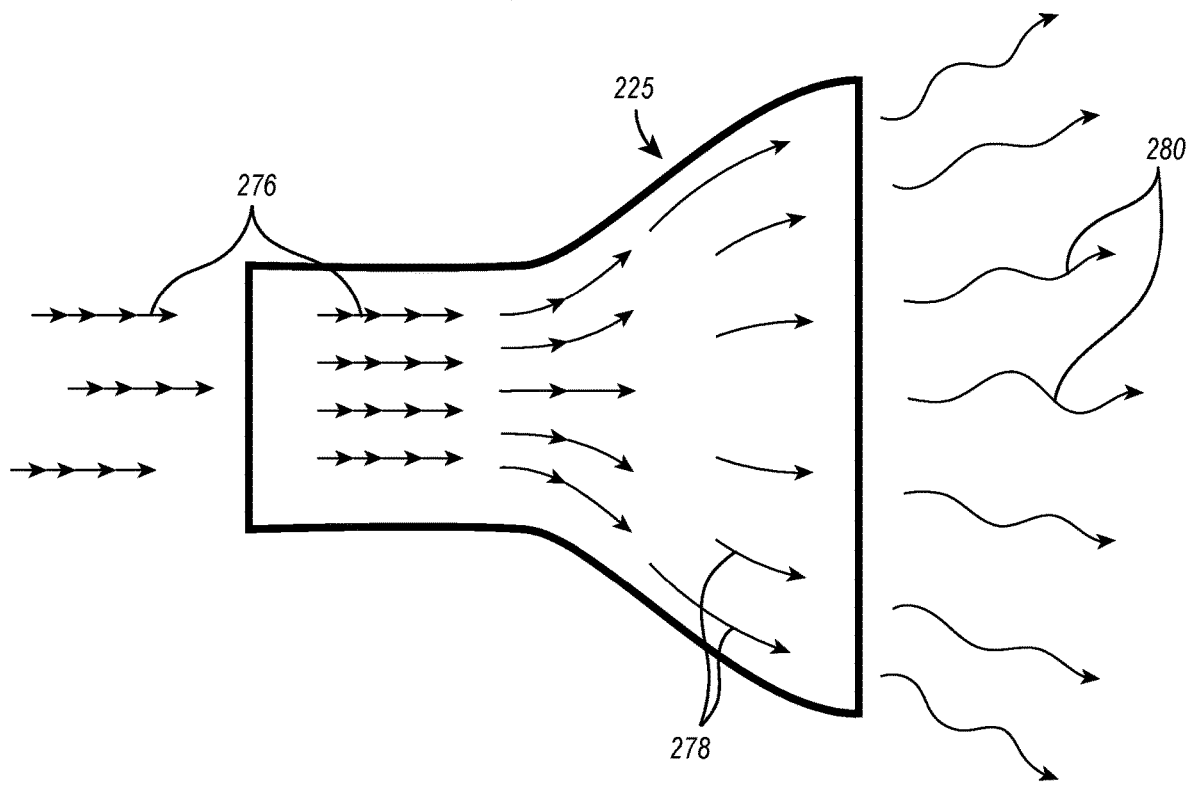
FIG. 7B illustrates a schematic of the diffuser illustrated in FIG. 7A.

FIGS. 7A and 7B illustrate an embodiment of an exhaust mechanism 214. The exhaust mechanism 214 may be configured to control or reduce the velocity of filtered air from the airflow path 208 exiting the smoke evacuation system 200 at the outlet port 224. The exhaust mechanism 214 may also be configured to decrease noise associated with high velocity filtered air exiting the outlet port 224. The exhaust mechanism 214 may help to reduce exit noise of the filtered air without baffling or redirecting flow causing an exit head pressure.

FIG. 7A illustrates a perspective view of an exhaust mechanism 214. The exhaust mechanism may be a diffuser 225. The diffuser 225 may include a plurality of vanes 274. The vanes 274 may be spaced apart and angled such that filtered air may flow out through the diffuser 225 between the vanes 274. The vanes 274 may be angled such that the vanes 274 force the air in a variety of directions upon exiting. FIG. 7B further illustrates how the diffuser 225 may decrease the velocity and noise of the filtered air exiting the system 200.

FIG. 7B illustrates a schematic of the diffuser illustrated in FIG. 7A. High velocity filtered air 276 may enter the diffuser in a substantially laminar flow pattern. The cross-sectional area of the diffuser 225 increases to expand the filtered air. The filtered air 278 exiting at the expanded cross-sectional area of the diffuser 225 decreases the velocity of the filtered air 278. The filtered air 280 then exits the diffuser through the plurality of vanes 274 shown in FIG. 7A so that the air is pushed in a variety of directions. Thus, the flow of the exiting filtered air 280 is no longer laminar. In this way, the diffuser 225 may reduce the velocity of the filtered air exiting the smoke evacuation system 200 at the outlet port 224, which in turn may reduce the noise of the exiting filtered air 280.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A smoke evacuation system, comprising:
    a housing at least partially surrounding an enclosure;
    an airflow path extending inside the enclosure from an inlet port to an outlet port of the smoke evacuation system;
    a motor disposed inside the enclosure and having a work output;
    a pump disposed inside the enclosure; and
    a cooling mechanism configured to induce airflow through the enclosure to cool the enclosure, the induced airflow being proportional to the work output of the motor, the cooling mechanism comprising:
        a first rotary element disposed within the airflow path;
        a second rotary element disposed outside the airflow path and within the enclosure; and
        a rotary element coupler, the rotary element coupler coupling the first rotary element to the second rotary element such that a rotation of the first rotary element causes the second rotary element to rotate.

2. The smoke evacuation system of claim 1, wherein the cooling mechanism comprises one or more openings in the housing of the smoke evacuation system.

3. The smoke evacuation system of claim 1, further comprising a filter and an exhaust mechanism, wherein the cooling mechanism comprises an opening in an airflow path through which air from outside the airflow path may pass into the airflow path, the opening being disposed between the filter and the pump or between the pump and the exhaust mechanism.

4. The smoke evacuation system of claim 3, wherein the exhaust mechanism reduces a velocity of a gas flowing through the airflow path.

5. The smoke evacuation system of claim 3, wherein the exhaust mechanism comprises a diffuser.

6. The smoke evacuation system of claim 1, wherein the cooling mechanism comprises an open juncture in the airflow path.

7. The smoke evacuation system of claim 6, the open juncture comprising:
    a first portion of the airflow path having a first diameter;
    a second portion of the airflow path having a second diameter that is larger than the first diameter; and
    the first portion at least partially extends into the second portion;
    wherein a space between the diameters of the first and second portion allows air from outside the airflow path to enter into the airflow path at the open juncture through the space.

8. The smoke evacuation system of claim 1, wherein:
    the first rotary element is configured to rotate in response to a pressurized gas flowing through the airflow path; and
    the rotation of the second rotary element is configured to circulate air throughout at least a portion of the enclosure to cool the motor and pump by convective heat transfer.

9. The smoke evacuation system of claim 8, wherein the rotary element coupler comprises one or more ball bearings and wherein the rotary element coupler is disposed in-line with the airflow path so as to prevent leaking at the rotary element coupler.

10. The smoke evacuation system of claim 1, further comprising a pressure release mechanism disposed at the inlet port or outlet port, the pressure release mechanism comprising a spring biased cover.

11. The smoke evacuation system of claim 10, wherein the spring-biased cover is disposed over an outlet port of the smoke evacuation system.

12. The smoke evacuation system of claim 10, wherein the spring-biased cover is disposed over an inlet port of the smoke evacuation system.

13. The smoke evacuation system of claim 1, further comprising a controller, wherein the controller causes the pressure release mechanism to reduce a pressure in the airflow path when a pressure inside the airflow path is equal to or greater than a defined pressure limit.

14. A smoke evacuation system, comprising:
    an inlet port;
    an outlet port;
    an airflow path extending between the inlet port and the outlet port;
    a housing at least partially surrounding an enclosure; and
    an exhaust mechanism near the outlet port and configured to diffuse air exiting at the outlet port to reduce exit noise without baffling or redirecting flow causing an exit head pressure, the exhaust mechanism comprising one or more vanes that are angled such that the exhaust mechanism has an expanding cross-sectional area, the one or more vanes being configured to force air in various directions as air exits the exhaust mechanism through the one or more vanes.

15. The smoke evacuation system of claim 14, wherein the exhaust mechanism comprises a diffuser.

16. The smoke evacuation system of claim 15, wherein the exhaust mechanism further comprises a pressure relief mechanism.

17. A smoke evacuation system, comprising:
    an inlet port;
    an outlet port;
    an airflow path extending between the inlet port and the outlet port; and
    one or more pressure relief mechanisms configured to regulate a pressure inside the airflow path, at least one of the one or more pressure relief mechanisms comprising a cover and one or more biasing members, the one or more biasing members being configured to (i) prevent the cover from closing the airflow path, (ii) bias the cover to a first open position when a pressure within the airflow path is below a predetermined level, and (iii) allow the cover to move to a second open position when a pressure within the airflow path is above the predetermined level.

18. The smoke evacuation system of claim 17, wherein at least one of the one or more pressure relief mechanisms is disposed at the inlet port.

19. The smoke evacuation system of claim 17, wherein at least one of the one or more pressure relief mechanisms is disposed at the outlet port.

20. The smoke evacuation system of claim 17, wherein the cover is a spring-biased cover.

* * * * *